United States Patent [19]

Long

[11] Patent Number: 5,342,355
[45] Date of Patent: Aug. 30, 1994

[54] ENERGY DELIVERING CAP ELEMENT FOR END OF OPTIC FIBER CONVEYING LASER ENERGY

[75] Inventor: Gary Long, Cincinnati, Ohio

[73] Assignee: Laser Centers of America, Cincinnati, Ohio

[21] Appl. No.: 963,206

[22] Filed: Oct. 19, 1992

[51] Int. Cl.$^5$ ............................................. A61B 17/36
[52] U.S. Cl. ........................................ 606/27; 606/15; 606/29
[58] Field of Search ................................... 606/13–16, 606/27–31, 37, 41, 45, 49, 7

[56] References Cited

U.S. PATENT DOCUMENTS

| | | | |
|---|---|---|---|
| 2,050,904 | 8/1936 | Trice | 606/29 |
| 3,434,476 | 3/1969 | Shaw et al. | 606/27 |
| 4,773,413 | 9/1988 | Hussein et al. | 606/28 |
| 4,832,979 | 5/1989 | Hoshino | 606/28 |
| 4,842,390 | 6/1989 | Sottini et al. | 606/15 |
| 4,978,346 | 12/1990 | Bentley | 606/28 |
| 5,087,256 | 2/1992 | Taylor et al. | 606/29 |
| 5,190,535 | 3/1993 | Daikuzono | 606/13 |

FOREIGN PATENT DOCUMENTS

| | | | |
|---|---|---|---|
| 8704611 | 8/1987 | PCT Int'l Appl. | 606/15 |
| 9007910 | 7/1990 | PCT Int'l Appl. | 606/15 |

OTHER PUBLICATIONS

Commercial Brochure "Bonding Capillaries", Small Precision Tools, Aug. 1990.

*Primary Examiner*—Stephen C. Pellegrino
*Assistant Examiner*—M. Peffley
*Attorney, Agent, or Firm*—Lowe, Price, LeBlanc & Becker

[57] ABSTRACT

A cap-like tip element is shaped and sized to fit over an energy-delivering distal end portion of an optic fiber conveying a flux of optic energy from a selected energy source. Optic energy emitted from an energy-emitting surface of the enclosed distal end of the optic fiber is received at a surface inside the tip element. In the preferred embodiment of the invention, the tip element is optically transmissive, and is shaped to facilitate precisely directed application of optic energy emitted therefrom. The material of the tip element is selected to be durable in prolonged use through repeated thermal cycling. In another aspect of the invention the tip element material is selected to be electrically conductive and is connected to an independently controlled electrical voltage source so that the tip element may be used as a cauterization tool by direct contact to selected tissue. In another aspect of the invention the material of the tip element is optically opaque, hence the received optic energy is converted into heat applicable by contact with tissue. In yet another aspect of the invention, a primary optic energy flux is focused into a small quantity of gas contained between a lens-shaped end of the optic fiber and the inside of the tip element, the primary optic energy flux being focused to generate a high temperature plasma emitting optic energy at a wavelength characteristic of the selected gas.

23 Claims, 4 Drawing Sheets

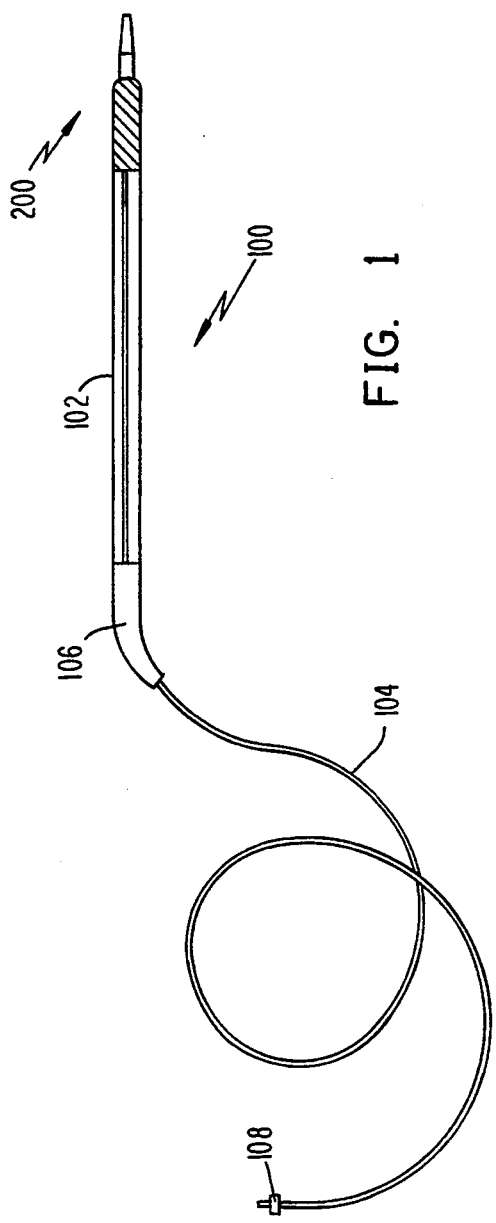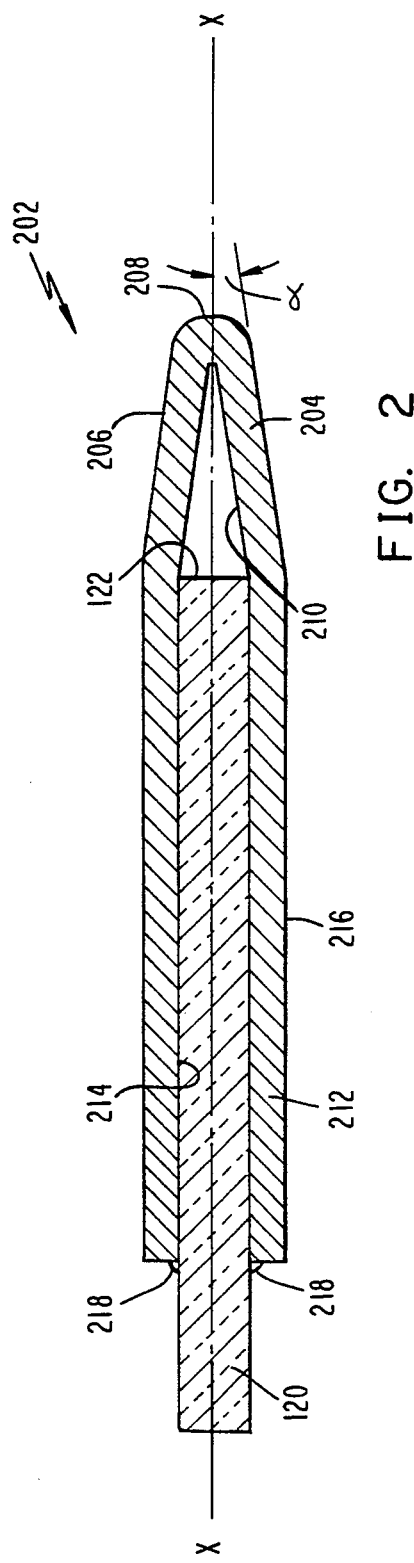

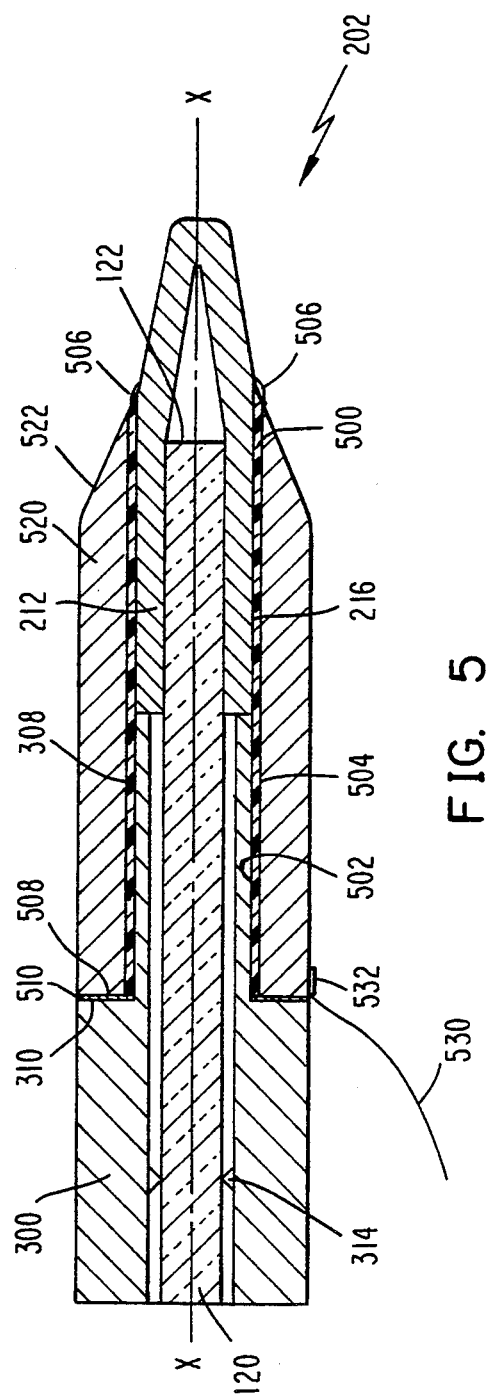
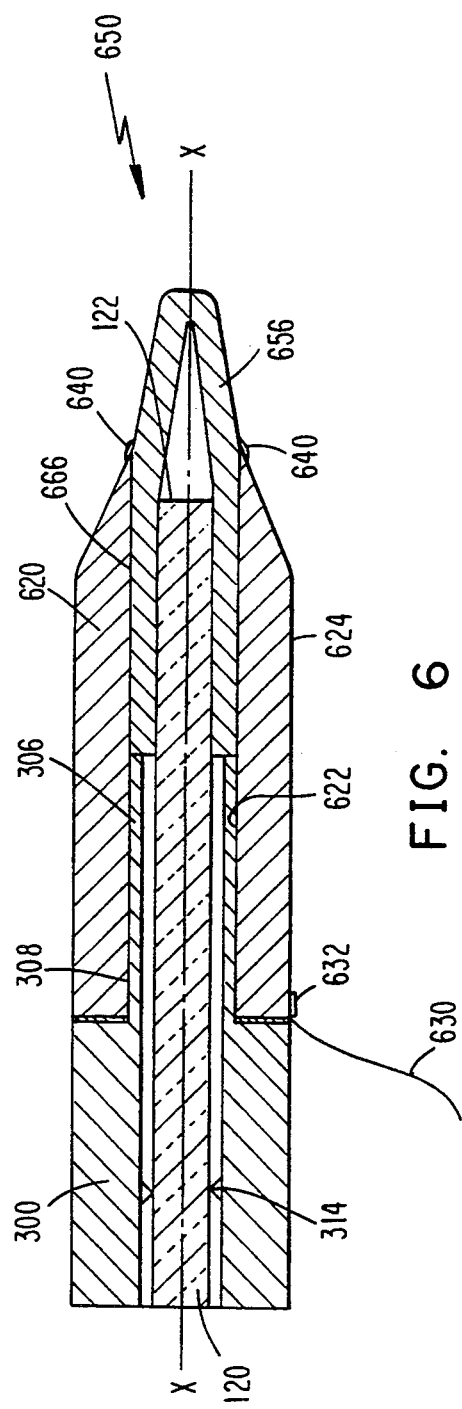
FIG. 5
FIG. 6

ENERGY DELIVERING CAP ELEMENT FOR END OF OPTIC FIBER CONVEYING LASER ENERGY

FIELD OF THE INVENTION

This invention relates generally to a durable energy delivering system utilizing laser light energy conveyed along an optic fiber, for example for surgical purposes, and more particularly to a durable energy delivering cap element fittable to a distal end of a single optic fiber conveying laser energy.

BACKGROUND OF THE PRIOR ART

Numerous surgical devices are known which utilize laser light as the primary form of energy conveyed by an elongate optic fiber and delivered it at selected locations for ablation or vaporization of tissue. Such devices can generally be divided into two principal categories: first, devices which have an end of the optic fiber itself shaped to emit laser energy in focussed form, e.g., for performing surgical incisions; and, second, devices which include in addition to the optic fiber a tip element which is heated by the laser energy. Such tip elements typically are formed of a ceramic material such as YAG, sapphire or silica, which materials are generally different from the material of the optic fiber. Both types of devices offer advantages and are deemed suitable for specific surgical applications, but both also pose certain problems in their manufacture and subsequent use. Laser surgical devices of these and other types are problems in their manufacture and subsequent use. Laser surgical devices of these and other types are becoming commonly available tools for a variety of surgical operations.

For use with each of these available tools, there are a variety of laser light energy sources capable of controllably delivering continuous or pulsed laser energy fluxes in selected wavebands, ranging from X-rays to infrared. Different advantages are realized by proper selection of the laser energy wavelengths and laser energy delivering tip designs. Copending applications U.S. Ser. Nos. 07/723,984; 07/723,987; 07/724,019; and 07/812,449 teach a variety of tip element forms, structures and improvements, each particularly suited to specific surgical applications.

A single optic fiber is often employed to delivery laser light energy emitted directly from a distal end contacted to tissue to perform incisions, coagulate blood, and/or cauterize severed blood vessels. Such an optic fiber end often degenerates and becomes structurally weak. This may be due to thermal cycling at very high and relatively low local temperatures in the course of repeated contacts with friable tissues.

If the optic fiber is connected to a separate tip element to avoid this, the material of the tip element must be such as to transmit the laser light energy very efficiently to the tissue. Also, Fresnel losses may occur in the interface between the optic fiber and the tip element where optic energy is transmitted between them. Copending applications U.S. Ser. Nos. 07/724,019 and 07/944,384 teach a simple solution to this problem. If the tip element material has a relatively low operating temperature, the same kind of physical degradation can occur as with a directly applied optic fiber end.

Furthermore, in the manner disclosed in the above-cited copending applications, e.g., U.S. Ser. No. 07/723,984, the tip element must be shaped not only to efficiently receive laser light energy from the optic fiber energy delivering end but also to accommodate to and permit certain types of surgical procedures. Such shaping of the energy delivering tip element, considering the materials involved, can be quite expensive even if economies of scale are realized in producing large numbers of such elements.

There is, therefore, an existing need for a way to deliver through a single optic fiber optic energy, e.g. from a laser source, in any of a variety of wavebands, precisely and repeatedly, over prolonged use at high efficiency. The present invention is intended to meet this need.

SUMMARY OF THE DISCLOSURE

A principal object of the present invention is to provide in a preferred embodiment a durable strong laser energy emitting tip element for efficiently delivering laser light energy at a precisely determined location.

Another object of this invention is to provide an energy delivering, cap-like, tip element fittable to a distal end of an optic fiber conveying laser light energy, the same tip element being selectively applicable by a user for electrocauterization in addition to incision.

A further related object of this invention is to provide a cap-like tip element fittable to a distal end of a laser light energy conveying single optic fiber, the tip element being inherently electrically conductive, to provide a single surgical tool which can be selectively operable for making incisions, for cauterizing incised blood vessels and for coagulating blood.

Yet another object of this invention is to provide a thin-walled, cap-like, tip element fittable to a distal end of an optic energy conveying single optic fiber, the tip element being formed by molding a selected material capable of absorbing optic energy delivered by the optic fiber to provide a high temperature heat flux by precisely applied contact at selected locations.

A related further object of this invention is to provide a thin-walled, cap-like, tip element fittable to a distal end of an optic energy transmitting single optic fiber, the tip element being formed of an optically transmissive material and having a thin layer of an optically absorbing material which absorbs transmitted optic energy to attain a high surface temperature for heating tissue by precisely applied contact thereto.

An even further object of this invention is to provide a cap-like energy delivery tip element fittable around a distal end of a laser light energy conveying single optic fiber, which generates within a small enclosed space a local plasma region in a selected gas maintained in energized state by laser light energy conveyed through the optic fiber.

In another aspect of this invention there is provided a method for generating a plasma by a focused flux of energy emitted from a lens-shaped end of an optic fiber to generate an electromagnetic radiation flux directable by a tip element enclosing the optic fiber energy-emitting end.

These and other related objects of this invention are realized in a preferred embodiment of the invention by providing a cap-like energy-delivering tip element, suitable for use with a laser surgical tool, shaped and sized to fit to and enclose a distal end portion and an energy-emitting end surface of an optic fiber transmitting energy from an optic energy source. The tip element has a hollow closed end portion having an outer energy-delivery surface of predetermined shape and size and a generally cylindrical open portion contiguous with said hollow closed end portion that is shaped and sized to receive therein the distal end portion and energy-emitting end face of the optic fiber. The inner surface of the closed end portion of the tip element receives energy emitted from the energy-emitting end surface of the optic fiber.

In another embodiment of this invention there is provided a system for precisely conveying a flow of optic energy from an optic energy source to an energy delivery site. It includes a length of an elongate optic fiber connectable at a first end to receive optic energy from the optic energy source and having a second end provided with an energy-emitting end surface for emitting optic energy conveyed through a length of said optic fiber. It also includes a cap-like tip element shaped and sized to enclose a distal end portion of the optic fiber, including the end surface. The tip element has a hollow closed end portion having an outer energy-delivery surface of predetermined shape and size and a generally cylindrical open portion contiguous with said closed end portion. The inside end surface of the closed end portion of the tip element receives optic energy emitted from the energy-emitting end surface of the optic fiber element.

In yet another aspect of this invention there is provided a system for generating a plasma by a specifically generated and directed flux of laser energy. The system has an elongate optic fiber element for conveying laser light energy to a distal end surface shaped to emit the conveyed laser light energy in a focused manner to a selected focal point. A cap-like element is shaped and sized to receive a distal length of the optic fiber and the distal end surface in such a manner as to define a space surrounding the focal point. A gas comprising atoms of a noble gas selected from a group consisting of argon, neon and xenon, occupies this space around the focal point. The focused emission of laser light from the optic fiber ionizes atoms of the selected noble gas at the focal point to generate a plasma thereat. This plasma radiates at a wavelength characteristic of the selected noble gas.

In a related further aspect of this invention, there is provided a method for protecting the physical integrity of an optic fiber formed of a first material and conveying an optic energy flux from an energy-emitting surface thereof when a distal end portion of the optic fiber adjacent to the energy-emitting surface is subjected to temperature cycling. The method requires covering of the distal end portion and energy-emitting surface of the optic fiber by a cap-like tip element formed of a second material. The tip element has a hollow closed end portion with an outer energy-delivery surface of predetermined shape and size and a generally cylindrical open portion contiguous with the hollow closed end portion shaped and sized to receive therein the distal end portion and energy emitting end face of the optic fiber. An inner surface of the closed end portion of the tip element receives energy emitted from the energy-emitting end surface of the optic fiber and the received energy is delivered from the outer energy-delivery surface of the tip element so that the effects of thermal cycling in use are essentially limited to the tip element.

BRIEF DESCRIPTION OF THE DRAWINGS

FIG. 1 schematically illustrates elements of an exemplary apparatus by which optic energy received from an optic energy source, e.g., a laser energy source, is conveyed to a hand-held tool comprising a laser light emitting tip element by which energy can be precisely applied for surgical procedures.

FIG. 2 is a longitudinal cross-sectional view of a cap-like tip element fitted to a distal end of a single elongate optic fiber in a preferred embodiment of this invention.

FIG. 5 is a longitudinal cross-sectional view of a structure generally similar to that illustrated in FIG. 4, wherein the tip element is recessed into a cone-ended metal sleeve by which a controlled current may be applied by the user to effect electrocauterization by contacting tissue.

FIG. 6 is a longitudinal cross-sectional view of a cap-like tip element fitted to a distal end of an optic fiber, wherein the tip element is made of an opaque electrically conductive material to enable delivery of a controlled electrocautery current by the user by contacting the tip element to tissue.

DESCRIPTION OF THE PREFERRED EMBODIMENTS

Figure 3:
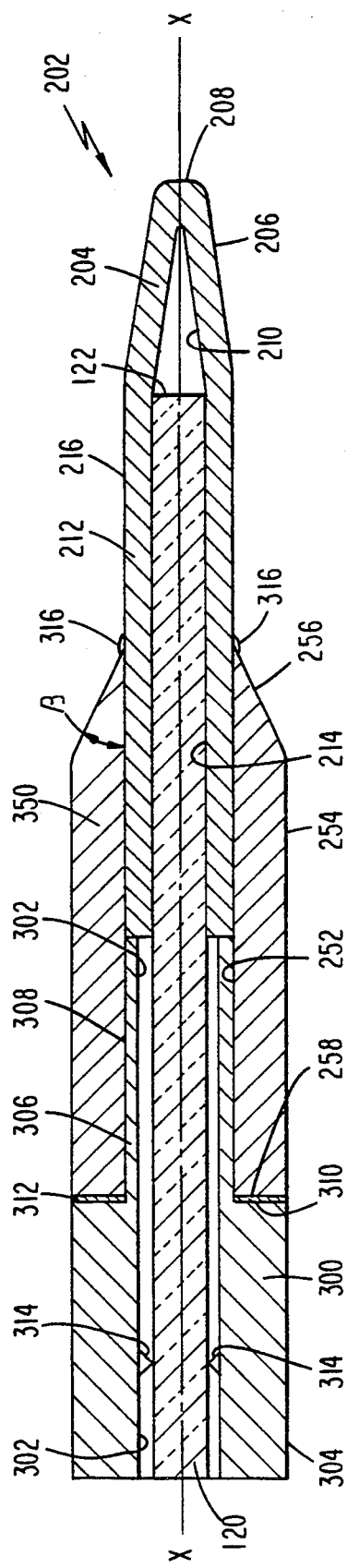
FIG. 3 is a longitudinal cross-sectional view of a cap-like optic energy transmitting tip element fitted to a distal end of a single energy conveying optic fiber and crimped in place into a metal connector with a thermally insulating sleeve.

A surgeon applying laser energy for surgical purposes, e.g., for making incisions through a patient's tissues, typically holds in his or her hand a lightweight, tool 100 into which is fitted an elongate assembly having a specifically shaped energized tip element to precisely apply energy by local contact with body tissues.

As best understood with reference to FIG. 1, such a hand-held surgical tool 100 typically has a slim elongate body 102 connected to a flexible element 104 at a junction 106. The flexible element 104, for example in known laser systems, typically comprises an outer tubular sheath protectively containing at least a suitable length of an optic fiber connected by a known junction 108 at one end to a source of laser light energy (not shown). In this manner, laser light energy of a suitable wavelength is received at junction 108 from a laser light source located at a convenient distance from the patient, and is conveyed via an optic fiber through flexible element 104, junction 106, and tubular element 102 to an energy applying tip element 200 of the hand-held surgical tool 100.

The term "optic energy" is used in the following detailed description of the apparatus and method of this invention to mean any waveband of electromagnetic radiation energy. It can range from the short wavelength end of the spectrum, e.g., X-rays, all the way to the much larger wavelength infrared radiation. Such optic energy may be in the form of coherent light, i.e., laser light, which may be preferred for many surgical purposes, but is not intended to be limited solely to laser light energy. The key is that the flux of optic energy be capable of allowing realization of the ultimate desired function, e.g., incision by gasifying or evaporating tissues.

Laser energy delivery systems, which are one variety of optic energy use systems used widely in medical applications in which different types of tissues are encountered, are becoming more and more application-specific. Different wavelengths of laser light can be applied to obtain correspondingly different effects on any given tissue. Similarly, faced with a need to use laser light energy of a different wavelength, e.g., in order to cut through a different type of tissue such as muscle or bone, at least with known systems the surgeon needs to use different laser surgical tools specifically designed to deliver laser energy at the selected wavelength.

There are however many applications where it is required only that a very high local temperature be generated, sufficient to essentially vaporize a variety of tissues, and that a sufficiently large local energy flux be available to do so in a precise manner. The actual emission a laser light energy flux from the tip element is not always desirable and may thus be avoided.

For practical reasons, a single optical fiber is often employed to deliver the laser light energy from an optic energy source to and through the surgical tool to the tip element which is of small dimensions but of a precisely selected shape. Typically, such a single optical fiber must transmit a substantial amount of the received optic energy, e.g., over 85%. There are certain inherent limitations when optic energy is thus delivered through a single fiber. Thus, if a certain power density of delivered laser energy is required to obtain a specific effect on tissue, then only the end surface of the fiber can be used to emit the energy. One consequence is that the optic fiber end becomes very hot. In frequent contact with friable tissues, intentionally or otherwise, it will experience repeated very rapid cooling. This thermal cycling is inevitable in use and tends to deteriorate the materials deemed most suitable for forming good optic fibers.

The present invention, in some of its embodiments as described more fully hereinbelow, provides a practical means of transducing optic energy conveyed via an optic fiber into a corresponding high temperature heat flux at a separate but cooperating tip element regardless of the wavelength of the primary flux of optic energy being employed or the tissue treated thereby. Such a form of this invention is ideally suited for use with single optical fibers delivering significant amounts of optic energy.

FIG. 2 illustrates the fundamental concept of this invention in its simplest physical embodiment. As already described, optic energy, e.g., laser light energy within a selected waveband, is conveyed from a source (not shown) through optic fiber 120 and is emitted from an energy-emitting end surface 122 thereof. Although this energy-emitting end surface 122 is shown as normal to the axis X—X of the distal end portion of optic fiber 120, this is not necessary, and other forms for such an energy-emitting end surface may be desirable. An embodiment incorporating a differently shaped end face is described later.

In the preferred embodiment per FIG. 2, a cap-like energy delivery tip element 202 has a closed forward end 204 with an energy-delivery outer surface 206 of selected shape and size. In this embodiment, the outer shape of this surface is intended to be merely exemplary and not as limiting, and has a generally conical form ending in a forwardmost surface portion 208 smoothly contiguous therewith. In the embodiment of FIG. 2, a substantial portion of the energy-delivery surface of tip element 202 is thus conical and subtends a half-cone angle "α", and is smoothly blends into forwardmost surface portion 208.

Optic energy, e.g., laser light energy within a selected waveband, is emitted from optic fiber end surface 122 and is received by an essentially conical inside surface 210. In certain embodiments, described later, this received optic energy is largely transmitted through the optically transmitting thickness of material between the inside surface 210 and the outside surface 206 (including portion 208) of the tip element 202. By suitable application of the closed forward end portion of tip element 202 to selected sites, a surgeon/user can apply the thus transmitted energy to the tissues of a patient. Such tissues will absorb the energy emitted from the energy-delivery surface 206 (including portion 208) of tip element 202 and become heated to a temperature high enough to gasify or vaporize the tissue material. The surgeon can thus perform incisions precisely.

Experience has established that, depending on the composition and mass density of tissues, it may be necessary to select the waveband and optic energy flux density for efficient incision. In other words, not all tissues respond in exactly the same manner to optic energy of a given waveband delivered at a particular rate. Given the surgical plan which the surgeon/user intends to follow, this can be most readily accomplished by selecting a suitable laser energy source (not shown) of which a variety are commercially obtainable and are available at most operating rooms where laser surgery is performed.

Tip element 202 has an open cylindrical elongate portion 212 which has inner and outer surfaces 214 and 216 respectively contiguous with inner and outer surfaces 210 and 206.

In the simplest embodiment per FIG. 2, the inner surface 212 of tip element 202 is formed to have a diameter only slightly larger than the outside diameter of optic fiber 120, so that the distal end portion of optic fiber 120 is closely received to be essentially coaxial with tip element 202. A small quantity of adhesive 218 is applied to bond tip element 202 to optic fiber 120 to ensure retention of the optic fiber within the tip element in the desired relative disposition.

The structure illustrated in FIG. 2 ensures that all the optic energy emitted from the optic fiber through its energy emitting end surface 122 is received within the closed end portion 204 of tip element 202. The material of tip element 202 must be carefully selected to be capable of prolonged service in use when subjected to frequent thermal cycling and forcible contact with hard tissues, both while emitting optic energy and at other times incidental to activities of the surgeon/user. It is also preferable that the outer energy-delivery surface 206 and its forwardmost end portion 208 each be smooth and contiguous with each other. Furthermore, to ensure the desired close fit of tip element 202 to optic fiber 120, the shape and size of the inside surface of tip element 202, comprising portions 210 and 212, must be manufactured with fairly high precision.

There exist industrial techniques for manufacturing small-bore, precisely-dimensioned, internally and externally smooth-surfaced, open and closed-ended, capillary-like elements of a variety of appropriate materials. The basic technique involves precision molding of materials having selected composition and such molding techniques are practiced to produce a variety of commercial products for forming ball and stitch bonds of the type needed in attaching fine leads to electronic microcircuits by, for example, SMALL PRECISION TOOLS, 1330 Clegg Street, Petaluma, Calif.

Among the materials believed to be particularly suitable for embodiments like the one illustrated in FIG. 2, i.e., one in which substantial amounts of optic energy is to be transmitted through and emitted from the closed end portion of the tip element, are what are generally recognized as ceramic materials: aluminum oxide ($Al_2O_3$), YAG, and zirconia. When formed by molding, these materials initially start out as very pure (99.99%+purity for $Al_2O_3$) fine powders in which the particles are within the size range 0.15–2.0 $\mu m$, with an average size of about 0.25 $\mu m$. The molding process is one known in industry as the "hot isostatic pressure" (HIP) process. This is the process utilized by the previously cited Small Precision Tools of California. The resulting product is very precisely dimensioned, has smooth contiguous inner and outer surfaces, and has the capability of transmitting over a few millimeters thickness of the material between 70%–80% of the received optic energy, especially in the infrared portion of the optic spectrum. To the naked eye, such tip elements appear to be translucent but, if the thickness of the material through which the optic energy is to be transmitted is kept relatively small, a substantial portion of the received optic energy is emitted through the closed end portion of the tip element.

The goal is to have a pragmatic solution to a clearly felt need, i.e., to provide a surgeon/user a durable and efficient optic energy delivering tip element. The small portion of the optic energy that is delivered from the optic fiber but is not emitted through the end portion of the tip element converts into heat within the tip element material. This heat must be continually removed from the tip element 202 and the length of optic fiber 120 which is received therein, to avoid overheating and untimely destruction of the device. An operating system intended for prolonged use must therefore provide a thermal path for that energy which is not transmitted through the tip element 202 but is converted into heat therein. Such an embodiment is illustrated in longitudinal cross-section in FIG. 3.

In the second embodiment per FIG. 3, optic fiber 120 is received within the open cylindrical portion 212 of the tip element 202 as before, i.e., such that the energy-emitting end surface 122 is disposed where the inside cylindrical surface 214 joins the inside surface 210 of the closed end portion, so that optic energy emitted from optic fiber end surface 122 is all received by the inside surface 210. In this embodiment, adhesive is not provided to directly bond tip element 202 to optic fiber 120. A different, heat-removing structure is provided instead. As best seen in FIG. 3, in this second embodiment, this is a thermally conductive open cylindrical connector element 250 which has an inside cylindrical surface 252 having a diameter only slightly larger than the outside surface 216 of the cylindrical portion of tip element 202. This facilitates a closely fitting reception of tip element 202 inside connector element 250.

Connector element 250 has an outer surface which consists of a cylindrical portion 254 and at a forward end a conical portion 256. The conical outer surface portion 256 subtends a half-cone angle "$\beta$" with respect to a common axis of tip element 202 and connector element 250, and "$\beta$" is preferably somewhat larger than "$\alpha$". The cylindrical outer surface 216 of tip element 202 is received to about the mid-point of inner cylindrical surface 252 of connector element 250.

Connector element 250 also has an annular end surface 258, preferably normal to its axis.

In addition, in the embodiment per FIG. 3, there is provided a length of metal tubing 300 which has an inside surface 302 of a diameter intermediate the diameters of optic fiber 120 and the outer cylindrical surface 216 of tip element 202. Metal tubing 300 has an outer cylindrical surface 304 of a diameter approximately equal to that of outer cylindrical surface 254 of connector element 250. A distal end portion 306 of metal tubing 300 has an outer cylindrical surface 308 having a diameter slightly smaller than the diameter of inside surface 252 of connector element 250 so as to be receivable within connector element 250 in a close sliding fit. In effect, therefore, metal tubing 300 has an extreme distal end portion 306 of a reduced outer diameter corresponding to the outer surface 308. This reduced diameter portion 306 has an inside cylindrical surface which is contiguous with and of the same size as the inside cylindrical surface 302 of the unreduced length metal tubing 300.

The reduced diameter portion 306 extends from the unreduced length of metal tubing 300 at an annular shoulder 310. The reduced diameter portion 306 separately has a length only slightly longer than that portion of connector element 250 not occupied by the cylindrical portion 212 of tip element 202. As a result, there is room for a relatively thin layer of adhesive material 312 to bond end surface 258 of connector element 250 to annular shoulder 310 of metal tubing 300. Tip element 202, likewise, is preferably adhered to the forwardmost conical end portion of connector element 250 by a small quantity of a suitable adhesive material 316.

Since direct adhesion between tip element 202 and optic fiber 120 is not employed in this embodiment, other means must be provided to ensure that optic fiber 120 remains in position as explained above and as illustrated in FIG. 3. One convenient technique for accomplishing this is to provide crimping, e.g., by the application of an outside force by crimping pliers or the like, to locally deform the wall of metal tubing 300 so that the inner surface 302 thereof contacts and grasps optic fiber 120 at locally deformed portions 314,314. This ensures that as the surgeon/user manipulates the above-described elements of tip assembly 200 within and at a forward end of surgical tool 100 the optical fiber will not become displaced out of its original/optimum position.

As will be appreciated, that portion of the optic energy emitted from end face 122 of optic fiber 120 which is not in fact transmitted out of the outer energy-delivery surface 206 (including end portion 208) of tip element 202 will be converted to heat. Depending on the optic energy flux, i.e., the power or energy/time, this non-transmitted energy will generate a corresponding thermal flux. In the embodiment of FIG. 3, because of the close fit between outer surface 216 of tip element 202 and inner surface 252 of thermally conductive connector element 250, this thermal energy is continually conducted away. Hence, both the exposed outer cylindrical surface 216 and the energy-delivery surface 206 (including portion 208) of the tip element 202 are not themselves maintained at a high temperature. Thermal energy thus conducted away from tip element 202 into connector element 250 is then conducted across cylindrical surfaces 252 (of connector element 250) and 308 (of the reduced diameter portion of metal tubing 300) into metal tubing 300 away from where it is produced. The assembly of elements thus described can be utilized for extended periods to perform surgical operations only with the energy transmitted through the thickness of the material of tip element 202 between the optic energy receiving inside surface 210 and the energy-emitting outer surface 206 (including portion 208) thereof.

In summary, in the second embodiment per FIG. 3, there is provided a thermal sink in addition to the basic combination of an optic fiber and a durable, selectively shaped, optic energy emitting tip element 202.

Experience has shown that there are certain surgical operations for which energy is best supplied to selected tissues solely in the form of heat by contact with a heated surface. Copending applications, U.S. Ser. No. 07/723,984 and 07/723,987 both describe assorted geometries and structures for tip elements for such purposes. These copending applications specifically teach techniques for forming surface layers on tip elements in a highly durable manner, these surface layers being formed of a selected material which has the ability to absorb the optic energy transmitted through the tip element material and to convert the same into surface heat. The portions of the cited copending applications specifically pertaining to such techniques for forming surface layers and for suitable materials from which to form them are expressly incorporated herein by reference. The incorporated techniques include both the "ion beam mixing process" as well as the "ion beam enhanced deposition process", as fully described in copending application U.S. Ser. No. 07/724,019. A preferred material for such purposes is titanium nitride (TiN).

Figure 4:
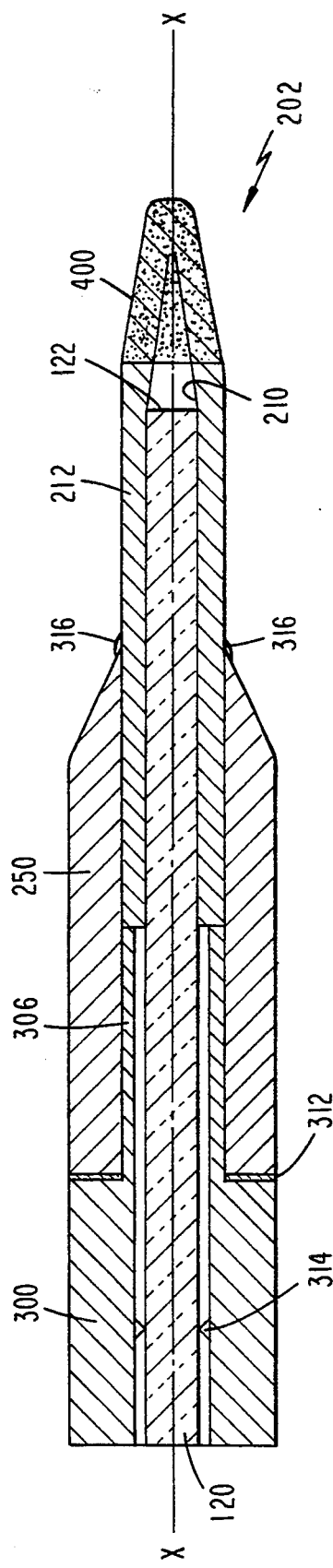
FIG. 4 is a longitudinal cross-sectional view of a cap-like tip element fitted to a distal end of an optic fiber, wherein a portion of the tip element has a surface treated to absorb optic energy to convert it into high temperature thermal energy applicable by contact with selected tissues.

FIG. 4 illustrates a third embodiment which is generally similar in relevant details to the embodiment illustrated in FIG. 3. The only significant structural difference between the second embodiment illustrated in FIG. 3 and the third embodiment illustrated in FIG. 4 lies in the provision in the latter of a surface layer 400 which extends over the energy-delivering distal end surface of closed portion 204 of tip element 202.

In use of the third embodiment per FIG. 4, optic energy emitted from energy-emitting end face 122 of optic fiber 120 passes in substantial portion through the thickness of the material of tip element 202 between its inside surface 210 and its outside surface 206 to reach the thin layer 400 which absorbs all of this transmitted energy and converts it to heat within a very small thickness, preferably within the range 2-50 μm. As will be readily appreciated, regardless of the waveband of the optic energy conveyed through optic fiber 120, if there is a substantial flux rate of optic energy in this manner the layer 400 will very quickly attain a very high temperature that is sufficient to gasify or vaporize selected tissues by precisely applied contact thereto.

Note that even though a very thin layer 400 is thus deliberately heated to a very high temperature, until and unless that heat is actually utilized to gasify or vaporize tissues by direct physical contact, only a small fraction of the heat will radiate away from layer 400 into the ambient atmosphere. Except for heat conducted away by direct external contact with layer 400, the optic energy flux conveyed through optic fiber 120 will all turn into thermal energy, hence it is very important to provide the thermal heat sink formed by the thermally conductive connector element 250 and the cooperating metal tubing 300, as described earlier with reference to FIG. 3.

Since this aspect of the invention, i.e., the provision of a heat sink, is exactly the same for both the second embodiment per FIG. 3 and the third embodiment per FIG. 4, a repetition of earlier provided details is not considered necessary.

As noted earlier, it is highly desirable to provide a surgeon the facility to make incisions and to also cauterize severed blood vessels with a single tool. This is particularly true where time is of the essence, e.g., under emergency conditions, or when working in a highly confined space where even relatively small collections of blood can seriously impede the surgeon's progress. The fourth embodiment, illustrated in FIG. 5, offers a solution to meet this need. The overall structure in this embodiment has much in common with that of the second embodiment per FIG. 3, with certain significant differences described more fully in the following paragraph.

In the fourth embodiment per FIG. 5 there is provided a cylindrical electrically and thermally nonconductive sleeve 500 which has an inside surface 502 and an outside surface 504. The diameter of inside surface 502 of sleeve 500 is only slightly larger than the outside diameter of the outer surface 308 of the reduced diameter portion 306 of metal tubing 300 and the diameter of outer cylindrical 216 of the open cylindrical portion 212 of tip element 202. Sleeve 500 is thus very closely fitted around the reduced diameter portion 306 of metal tubing 300 and, preferably, around the entire length of cylindrical portion 212 of tip element 202. The diameter of outside surface 504 of sleeve 500 is only slightly smaller than the diameter of inside surface 252 of an electrically conductive connector element 520 which is very similar to the connector element 250 of FIG. 3 in shape.

The presence of sleeve 500 ensures that the outer surface 522 of connector element 520 will be relatively cool so that inadvertent contact of tissue therewith will not heat that tissue unduly. This surface 522 will be applied only for generating an electrocautery current to flow into contacted tissue by independently controlled application of a voltage via wire 530 as explained below.

The length of connector element 520 is selected to be such that the end of its conical forward surface 556 is located where the outer cylindrical surface 216 blends in with the energy-emitting outer surface 206 of tip element 200. A small amount of a suitable adhesive material 506 is provided to adhere sleeve 500 to tip element 200 and to the forwardmost edge of connector element 500. Connector element 500 is also adhered at its rearmost end surface 508 to similarly sized and oriented shoulder 310 of metal tubing 300 by a layer 510 of a suitable adhesive material.

As in the second embodiment per FIG. 3, crimping of metal tubing 300 is conveniently employed to grasp and hold in place optic fiber 120 in place so that its energy-emitting end face 122 emits optic energy to inside surface 210 of the closed end portion 204 of tip element 200.

In addition, an electrical wire 530 is connected to electrically conductive connector element 520 at 532. This wire 530 is preferably connected to a positive terminal of a monopolar electrocautery generator of known kind, preferably via a foot-controlled switch independently operable by the surgeon/user, to enable the application of a selected voltage to connector element 520. This is best understood with reference to FIG. 8.

With the fourth embodiment per FIG. 4, as just described, a surgeon/user can utilize optic energy conveyed via fiber 120, emitted through its end face 122 and transmitted out of the outer energy emitting surface 206 (including portion 208) of optically transmissive tip element 200 to perform conventional incisions as with the previously described other embodiments. In addition, while applying a controlled voltage via wire 530 the surgeon/user can selectively contact the outer surface 522 of connector element 520 to cause an electrocautery current to flow into the tissues of a patient 1100 at a selected point of contact if the patient is also connected to an opposite pole of the electrocautery generator. In other words, by exercising independent control over the flux of optic energy conveyed via optic fiber 120 and on an electrocauterization current applied by contacting surface 522 to selected tissue, the surgeon can with a single tool rapidly and precisely perform incisions and cauterize tissues very efficiently and with a minimum of distraction. A convenient form of control for applying electrocauterization current in this manner comprises a foot-operated switch connected to the electrocautery generator. A known arrangement of this type is described in copending application U.S. Ser. No. 07/812,449, and relevant details thereof are expressly incorporated herein by reference.

Figure 8:
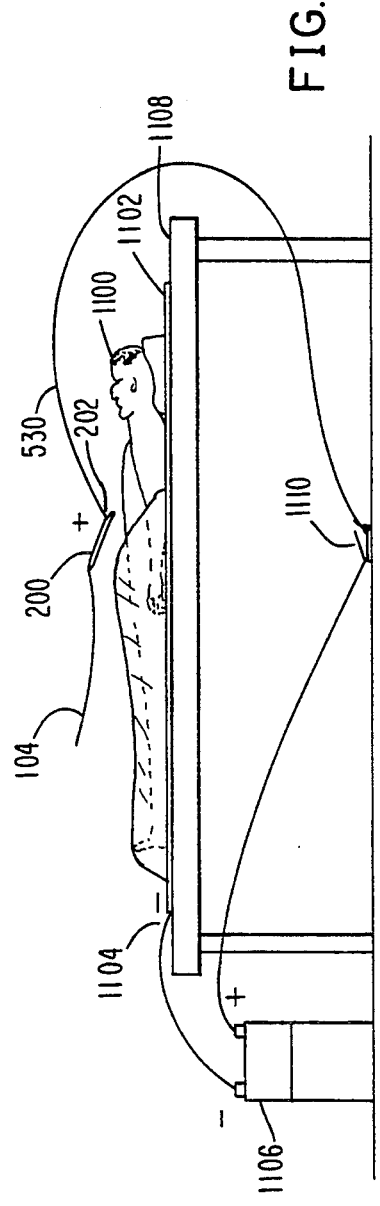
FIG. 8 is a schematic view illustrating how a patient may be supported in electrically conductive contact with an electrocautery system that can be used with certain embodiments of this invention as described herein.

Reference may be had at this point to FIG. 8 which illustrates schematically a patient 1100 lying in electrically conductive contact on a surface of a large conductive pad 1102 electrically connected at a point 1104 to, for example, the negative terminal of an electrical voltage source 1106. Electrically conductive pad 1102 is supported on an upper surface of an operating table 1108 which may, preferably, be commonly grounded therewith. Through a user-operated and preferably foot-actuated switch 1110, the positive terminal of electrical voltage source 1106 may thus be connected to the cauterization portion of the tip assembly in hand-held tool 200 by which the surgeon may apply the requisite cauterization current to a cut blood vessel of the patient.

Another form of a unified surgical/cauterization tool is provided in the fifth embodiment of the present invention, as illustrated in longitudinal cross-section in FIG. 6. In this embodiment, metal tubing 300 has a distal end portion 306 with an outside surface 308 of reduced diameter, in the same manner as in the second embodiment as illustrated in FIG. 3.

The fifth embodiment per FIG. 6 has a connector element 620 with an inside cylindrical surface 622 of a diameter only slightly larger than the diameter of reduced diameter portion 308 of metal tubing 300 and the outside diameter 666 of the open cylindrical portion of tip element 650 which is fitted to the distal end of an optic fiber 120 as in the previous embodiments per FIGS. 3, 4 and 5. Connector element 620 is adhered to tip element 650 by the application of a suitable adhesive at 640. Preferably, the forwardmost conical portion of external surface 624 of connector element 620 ends where the energy-applying outer surface 656 at the closed energy-applying forward portion of tip element 650 joins the open cylindrical portion thereof. An electrical wire 630 is connected at 632 to electrically conductive connector element 620, another end of wire 630 being connected to a monopolar electrocautery generator as described in explaining the fourth embodiment with reference to FIG. 5. See also FIG. 8.

The material of tip element 650 is one which has an inherent capability for absorbing all optic energy emitted from end face 122 of optic fiber 120. Such a tip element 650 may be molded in the same manner as the optically transmissive tip element of the second embodiment, except that the material instead of being a finally translucent ceramic would be either titanium carbide (TIC) or tungsten carbide (WC) both of which are optically opaque and electrically conductive. Either of these materials may be employed, preferably in the form of a fine powder in which the particles have an average size of approximately 0.3 $\mu$m within the size range 0.15-2.0 $\mu$m. Such fine micrograin-type powders of these materials are commercially available. Molding, as described above, can be employed to produce the necessary precision-molded tip elements generally having the same shape and size as the optically transmissive tip element 202 employed in combination with the other elements described with reference to FIG. 3. Repetition of such details, therefore, is not considered necessary for an understanding of this embodiment.

The key fact is that a tip element formed of titanium carbide or tungsten carbide, while having the same shape and size as the light transmissive tip elements per either FIGS. 3 or 4, would absorb all the optic energy emitted from end face 122 of optic fiber 120. Such "opaque" tip elements would become heated and, by application of their smooth outer surfaces, could be utilized in exactly the same manner as the third embodiment illustrated in FIG. 4. It is believed that it would generally be less expensive to manufacture such an "opaque" tip element then it would be to form a tip element 400 (see FIG. 4), which requires the formation of a specific energy-absorbing outer layer per the third embodiment described above. The technique for using either the "opaque" tip element or the "layered" tip element per the third embodiment is essentially similar.

In use, the fifth embodiment per FIG. 6 allows a surgeon/user to direct and apply a high temperature heat flux to perform incisions in the conventional manner. However, when an incised blood vessel is to be electrocauterized, the surgeon simply terminates the optic energy flux and, instead, applies a controlled electrical voltage through wire 630 to electrically conductive connector element 620 and thereby to the tip element 650 which is physically contacted to a selected site in the patient's tissue. The ancillary equipment, e.g., the monopolar electrocautery generator, incidental wiring, and independent controls to operate the same, are all as schematically illustrated in FIG. 8 the use of which is described in the material incorporated by reference.

Persons of ordinary skill in the art will immediately appreciate that an obvious variation of the embodiments illustrated in FIGS. 5 and 6 is to make the cap-like tip element in FIG. 5 optically opaque, i.e., like element 650 (made of TiC or WC) per the sixth embodiment per FIG. 6. In such a structure the electrocauterization current would flow via surface 522 of the connector element instead of the thermal energy applying surface 657 of opaque tip element 650. Insulating sleeve 500 would perform as usual.

Figure 7:
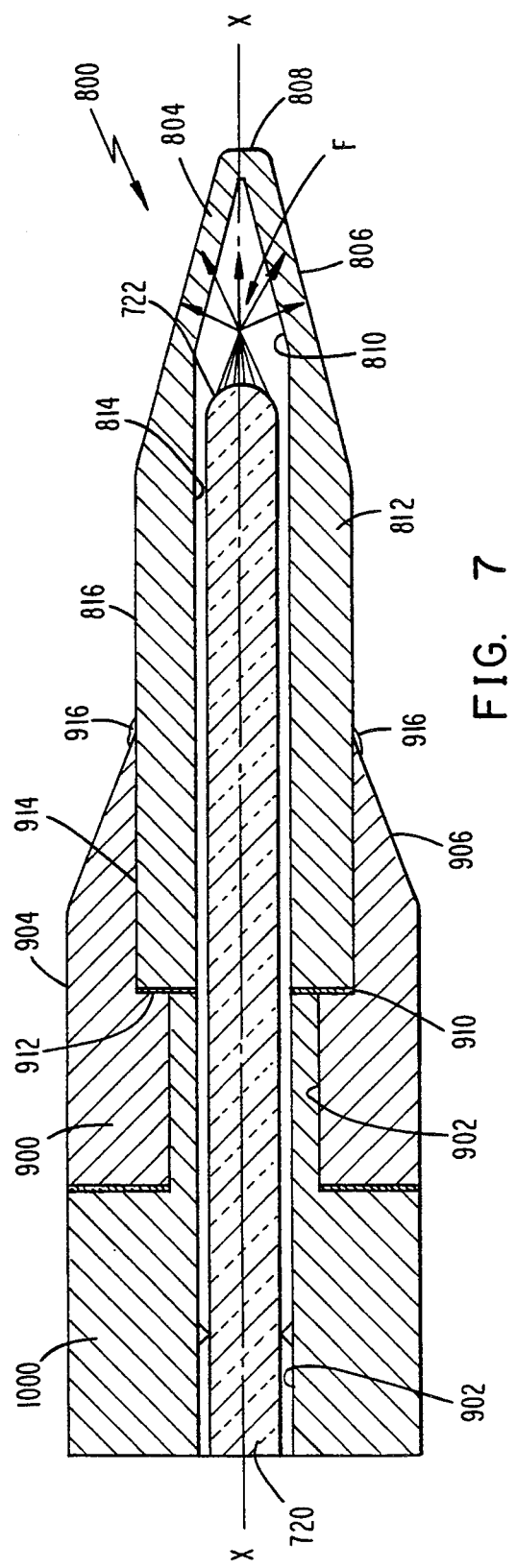
FIG. 7 is a longitudinal cross-sectional view of another aspect of this invention, wherein a cap-like energy delivering tip element covers a distal end of a laser light energy conveying single optic fiber in such a manner as to form a small compartment filled with a selected gas which is ionized by laser light energy delivered through a shaped end of the optic fiber and maintained in a plasma state to emit a radiant flux of energy.

FIG. 7 illustrates in longitudinal cross-section the sixth embodiment of this invention, in which a primary flux of optic energy is conveyed along an optic fiber 720 connected at one end to an optic energy source (not shown). An energy-delivering distal end of the optic fiber is preferably shaped to have a convex, smooth, curved, lens-like energy-emitting surface 722. The optically transmissive tip element 800, geometrically generally similar to the earlier described tip elements, has a closed energy-delivery portion 804 having an outer energy-emitting surface 806 which is smoothly contiguous with a forwardmost surface portion 808. This forward energy-emitting portion of the tip element 800 has an inside surface 810. The energy-emitting closed portion 804 is structurally contiguous with a generally cylindrical elongate portion 812 which has an inside surface 814 contiguous with inside surface 810, as well as an outer cylindrical surface 816 contiguous with surface 806. The inside cylindrical surface 814 is a little larger in diameter than the outer diameter of optic fiber 720. Consequently, a small annular cylindrical space is left around the distal end portion of optic fiber 720.

The embodiment per FIG. 7 also has a connector element 900 which preferably has a central aperture with a cylindrical inside surface 914 having a diameter slightly larger than the diameter of outside surface 816 of tip element 800. Connector element 900 has an outer surface comprising a cylindrical portion 904 and a conical front portion 906. Tip element 800 is received within connector element 900 in a close fit. An adhesive material 910 is provided to connect tip element 800 inside connector element 900 at an annular surface 912 which separates its inside cylindrical surface 902 from the relatively larger inside cylindrical surface 914 surrounding a portion of the tip element. Connector element 900 may be further connected to tip element 800 by the provision of adhesive material at 916 to ensure a gas-tight connection.

Connector element 900 may be fitted to a length of metal tubing 1000 comparable in form and function to metal tubing 300 as described above with reference to FIGS. 3, 4, 5 and 6. Because of the extensive similarities of metal tubing 1000 to that of metal tubing 300 described in explaining the earlier embodiments, a detailed description thereof is not considered necessary. Metal tubing 1000 may be locally crimped to hold in place the distal end portion of optic fiber 720.

What is unique and different about the embodiment per FIG. 7 is that the forwardmost end surface 722 of the optic fiber 720 is shaped so that the material of the optic fiber itself functions as a convex lens to focus emitted optic energy to a focal point "F" located forwardly of the convexly curved energy-emitting surface 722. This "focal point F", while not necessarily meeting the mathematical definition of a "point" is nevertheless a very small volume, so that the optic energy emitted from optic fiber 720 is, in effect, very highly intensified in this small volume.

A noble gas, e.g., argon, neon or xenon, is provided to occupy the volume between the curved end face 722 of optic fiber 720 and essentially the inside surface 810 and the immediately contiguous portion of inside surface 814 of tip element 800. The gas can be provided from any conventional pressurized source of the gas (not shown) through a small-bore gas line (not shown) extending along flexible element 104 and into the annular space surrounding optic fiber 720, through the use of any conventional fittings, valves and the like (not shown). In this manner, the small volume of space at and immediately surrounding focal point "F" will contain a predetermined population density of noble gas atoms. Upon the provision of a sufficient flux of optic energy through optic fiber 720, the focusing effect of lens-shaped end face 722 will cause a highly intense energy transfer to the atoms of the selected noble gas at focal point "F". This input of energy will locally raise the temperature of the selected atoms to a value sufficient to ionize such atoms. The continuous delivery of optic energy will ensure maintenance of this ionized region which, in effect, constitutes a highly energetic plasma state of the selected noble gas.

Note that it is the rate at which optic energy is delivered to focal point "F" which is determinative of the generation and maintenance of a plasma of the selected noble gas, and not the wavelength or waveband of such focused optic energy flux. However, since each noble gas in its plasma state will radiate energy at a characteristic wavelength, the result of generating the small local plasma region is to create a source of optic energy emitted at a wavelength characteristic of the selected noble gas only.

As indicated by the bunched arrows in FIG. 7, this radiation from the plasma at focal point "F" will be emitted to reach inside surface 810 of tip element 800. Depending on the transmissive capability of the material of tip element 800, it will pass through and be emitted from outer surface 806 (including portion 808) of the tip element 800. In this manner, available optic energy of almost any wavelength can be readily converted into an optic energy output at a wavelength characteristic of a selected noble gas. Clearly, there may be other practical uses for a continuously generated and maintained small volume of a selected plasma powered and sustained by a focused optic energy pulse in the very simple structure described above.

Note that, as in the structure of the fourth embodiment per FIG. 5, one could connect an electrical wire (not shown for simplicity) and thereby apply an electrocauterization current through an electrically conducting connector element 900, to thereby provide a single unified tool capable of emitting optic energy from the forwardmost portion for precision and, simultaneously, enabling the application of an electrocauterization current by contacting the patient's tissues with the outside surface 904 of connector element 900.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein. In particular, it should be understood that individual aspects, such as the provision of an electrocauterization current and the like, can be combined with assorted combinations of geometric features, etc., as deemed most suitable for specific applications of this invention.

What is claimed is:

1. A cap-like energy-delivery tip element, suitable for use with a laser surgical tool, shaped and sized to permanently fit to and enclose a distal end portion and an energy-emitting end surface of an optic fiber transmitting energy from an optic energy source, comprising:
- a hollow closed end portion having an outer energy-delivery surface of predetermined shape and size; and
- a generally cylindrical open portion contiguous with said hollow closed end portion, shaped and sized to closely receive therein and permanently attach to the distal end portion and energy-emitting end face of the optic fiber,
- whereby an inner surface of the closed end portion of the tip element receives energy emitted from the energy-emitting end surface of the optic fiber,
- wherein said tip element is molded from a material comprising particles which before said molding are within a size range 0.15–2.0 μm,
- at least said closed end portion of said tip element comprises an opaque material which absorbs said received optic energy and converts the same to thermal energy, whereby said outer energy-delivery surface thereof is heated to a predetermined high temperature, said opaque material being electrically conductive, and
- said tip element is electrically conductive, and comprises
- voltage application means connected to said electrically conductive tip element to enable controlled provision of a predetermined first voltage thereto.

2. The tip element according to claim 1, wherein:
said voltage application means further comprises means for electrically connecting to an object held at a predetermined second voltage by said voltage application means,
whereby physical contact by said outer energy-delivery surface of said tip element at a selected location on said object enables passage of a controlled electrical current thereat due to a voltage difference between said first and second voltages.

3. A system for precisely conveying a flow of optic energy from an optic energy source to an energy delivery site, comprising:
- a length of an elongate optic fiber connectable at a first end to receive optic energy from said optic energy source and having a second end provided with an energy-emitting end surface for emitting optic energy conveyed through a length of said optic fiber;
- a cap-like tip element shaped and sized to securely attach to and closely fit to and enclose a distal end portion of said optic fiber including said end surface thereof, said tip element comprising a hollow closed end portion having an outer energy-delivery surface of predetermined shape and size and generally cylindrical open portion contiguous with said closed end portion, whereby an inside end surface of said closed end portion of the tip element receives said optic energy emitted from the energy-emitting end surface of the optic fiber element, said generally cylindrical open portion of said tip element being formed to closely fit around said second end of said optic fiber to receive a length thereof such that the energy-emitting end surface of the optic fiber is located at a junction between said generally cylindrical open portion and said closed end portion of said tip element;
- a length of metal tubing having an inner diameter larger than an outside diameter of the optic fiber, and an outside diameter larger than an outside diameter of said tip element, a first length of said metal tubing at one end having a reduced diameter which is substantially equal to said outside diameter of said tip element, a junction of said first length of reduced diameter with a portion of the metal tubing having an unreduced diameter comprising an annular surface;
- a connector element of a second length longer than said first length, having an inner diameter slightly larger than said outer diameter of said tip element and said reduced diameter of said first length of said metal tubing, said connector element having an outside diameter substantially equal to said outside diameter of said metal tubing, a forward end of said connector element being formed to have a conical surface;
- first means for connecting said annular surface of said metal tubing to a second end of said connector element with said reduced diameter portion of said metal tubing received within said connector element; and
- second means for connecting said connector element to an outside surface of said cylindrical portion of said tip element received therein to abut said reduced portion of said metal tubing; and
- wherein a distal end portion of said optic fiber extends through said metal tubing, inside said connector element, and into said cylindrical open portion of said tip element so that an energy emitting end surface of said optic element is disposed at a junction between said open cylindrical portion and said closed end portion of said tip element.

4. The system according to claim 3, wherein:
said first and second means for connecting each comprise a respective adhesive material.

5. The system according to claim 3, wherein:
said metal tubing is crimped so that an inside surface thereof is locally deformed to grasp and hold said optic fiber.

6. The system according to claim 3, further comprising:
an optic energy absorbing layer provided at said outer energy-delivery surface of said tip element, to absorb optic energy emitted from said energy-delivery end surface of said optic fiber and to convert the same to heat and thereby raise the temperature of said optic energy absorbing layer.

7. The system according to claim 6, wherein:
said metal tubing is crimped so that an inside surface thereof is locally deformed to grasp and hold said optic fiber.

8. The system according to claim 3, further comprising:
a cylindrical sleeve of a thermally insulating material, disposed intermediate an inside surface of said connector element and the outside surfaces of both said cylindrical portion of said tip element and said reduce diameter length of said metal tubing.

9. The system according to claim 8, wherein:
said thermally insulating sleeve is formed of tetrafluoroethylene (TFE).

10. The system according to claim 8, wherein:
said metal tubing is crimped so that an inside surface thereof is locally deformed to grasp and hold said optic fiber.

11. The system according to claim 8, wherein:

said open cylindrical portion of said tip element is of a length such that said conical surface of said first end of said connector element ends at an outside surface junction between said open cylindrical portion and said energy-delivery outer surface of said tip element.

12. The system according to claim 3, wherein:
said tip element comprises a first electrically conductive material, and said connector element comprises a second electrically conductive material, said metal tubing, said connector element, and said tip element cooperating to provide an electrically conductive path from said metal tubing to said outer energy-delivery surface of said tip element.

13. The system according to claim 12, further comprising:
voltage application means connected to one of said metal tubing, said connector element and said tip element, to enable the provision of a predetermined controlled first voltage thereto.

14. The system according to claim 13, further comprising:
means for electrically connecting said voltage application means to an object to thereby apply to said object a different second voltage,
whereby physical contact by said outer energy-delivery surface of said tip-element at a selected location on said object enables passage of a controlled electrical current at said location, corresponding to a voltage difference between said first and second voltages.

15. The system according to claim 14, wherein:
said metal tubing is crimped so that an inside surface thereof is locally deformed to grasp and hold said optic fiber.

16. A system for precisely conveying a flow of optic energy from an optic energy source to an energy delivery site, comprising:
a length of an elongate optic fiber connectable at a first end to receive optic energy from said optic energy source and having a second end provided with an energy-emitting end surface for emitting optic energy conveyed through a length of said optic fiber;
a cap-like tip element shaped and sized to securely attach to and closely fit to and enclose a distal end portion of said optic fiber including said end surface thereof, said tip element comprising a hollow closed end portion having an outer energy-delivery surface of predetermined shape and size and a generally cylindrical open portion contiguous with said closed end portion, whereby an inside end surface of said closed end portion of the tip element receives said optic energy emitted from the energy-emitting end surface of the optic fiber element;
a length of metal tubing having an inner diameter larger than an outside diameter of the optic fiber, and an outside diameter larger than an outside diameter of said tip element, a first length of said metal tubing at one end having a reduced diameter which is substantially equal to said outside diameter of said tip element, a junction of said first length of reduced diameter with a portion of the metal tubing having an unreduced diameter comprising an annular surface;
a connector element of a second length longer than said first length, having an inner diameter slightly larger than said outer diameter of said tip element and said reduced diameter of said first length of said metal tubing, said connector element having an outside diameter substantially equal to said outside diameter of said metal tubing, a forward end of said connector element being formed to having a conical surface;
first means for connecting said annular surface of said metal tubing to a second end of said connector element with said reduced diameter portion of said metal tubing received within said connector element; and
second means for connecting said connector element to an outside surface of said cylindrical portion of said tip element received therein to abut said reduced portion of said metal tubing, wherein a distal end portion of said optic fiber extends through said metal tubing, inside said connector element, and into said cylindrical open portion of said tip element so that an energy emitting end surface of said optic element is disposed at a junction between said open cylindrical portion and said closed end portion of said tip element; and
a selected gas comprising atoms of a noble gas selected from a group of noble gases consisting of argon, neon and xenon provided in a space between said energy-emitting end surface of the optic fiber and an inside surface of said closed end portion of said tip element,
wherein said energy-emitting end surface of said optic fiber has a convex curved shape whereby optic energy emitted therefrom is focused at a focal point within said gas, said gas being heated by said focused emitted energy to a temperature sufficient to ionize said atoms of said selected noble gas to a plasma state thereof to thereby generate an electromagnetic radiation at a wavelength characteristic of said selected noble gas, said electromagnetic radiation being received at an inside surface of said closed end portion of said tip element for emission from said outer energy-delivery surface thereof.

17. The system according to claim 16, comprising
means for providing said selected noble gas along and past an outer surface of said optic fiber through said metal tubing, said connector element, and said open cylindrical portion of said tip element to said space.

18. The system according to claim 17, wherein:
said metal tubing is crimped so that an inside surface thereof is locally deformed to grasp and hold said optic fiber.

19. A system for generating a plasma by a focused flux of laser energy, comprising:
an elongate optic fiber element for conveying laser light energy to a distal end surface shaped to emit said conveyed laser light energy in a focused manner to a selected focal point;
a cap-like element shaped and sized to receive a distal length of the optic fiber and said distal end surface in such a manner as to define a space surrounding said focal point communicating with an annular cylindrical space around the distal end portion of the optic fiber; and
a gas, provided to said space via said annular space and comprising atoms of a noble gas selected from a group consisting of argon, neon and xenon, occupying said space,
whereby said focused emission of laser light from said optic fiber ionizes said atoms of said selected noble gas at said focal point to generate a contained plasma thereat which emits electromagnetic radiation at a wavelength characteristic of the selected noble gas.

20. A method for transforming a primary flux of optic energy, provided within a first waveband through an optic fiber, into a directed flux of optic energy of a selected wavelength, comprising the steps of:

shaping an energy-delivery distal end of the optic fiber to serve as a lens for focussing said primary flux emitted therefrom at a focal point located at a predetermined distance from said distal end;

disposing the distal end of the optic fiber inside a cap-like tip element formed of an optically transmissive material, the tip element being thin-walled and shaped so as to provide a hollow space surrounding said focal point;

providing atoms of a selected gas to be contained in said hollow space;

delivering said focussed primary flux of optic energy from said optic fiber to said gas atoms at said focal point to ionize the gas atoms and thereby generate a flux of transformed optic energy at a wavelength characteristic of the selected gas; and directing said generated optic energy flux through said tip element.

21. The method according to claim 20, wherein:
said tip element comprises a material selected from a group of materials consisting of aluminum oxide ($Al_2O_3$), YAG and zirconia.

22. The method according to claim 21, wherein:
said tip element in a portion receiving said generated optic energy flux has walls of a thickness and optical transparency such as to allow transmission of at least 50% of the generated optic flux from an outside surface of the tip element.

23. The method according to claim 20, wherein:
said selected gas comprises atoms of a noble gas selected from a group consisting of argon, neon and xenon.

* * * * *